United States Patent [19]

Yokozeki et al.

[11] Patent Number: 4,755,466
[45] Date of Patent: Jul. 5, 1988

[54] PROCESS FOR PRODUCING L-PHENYLALANINE

[75] Inventors: Kenzo Yokozeki; Norimasa Onishi, both of Kawasaki; Hideo Kano, Yokosuka; Yoshiteru Hirose, Kamakura, all of Japan

[73] Assignee: Ajinomoto Co., Inc., Tokyo, Japan

[21] Appl. No.: 697,576

[22] Filed: Feb. 1, 1985

[30] Foreign Application Priority Data

Feb. 3, 1984 [JP] Japan ................................. 59-18869
Jul. 31, 1984 [JP] Japan ............................... 59-161216
Oct. 15, 1984 [JP] Japan ............................... 59-215962

[51] Int. Cl.[4] .......................... C12N 1/14; C12N 1/16; C12P 13/22; C12R 1/645
[52] U.S. Cl. .................................... 435/108; 435/254; 435/255; 435/911; 435/913
[58] Field of Search ............... 435/108, 191, 193, 254, 435/255, 911, 913

[56] References Cited

U.S. PATENT DOCUMENTS 4,562,151 12/1985 Kishore ............................... 435/108
4,584,269 4/1986 Vollmer et al. ...................... 435/108
4,600,692 7/1986 Wood et al. ......................... 435/108
4,681,850 7/1987 McGuire ............................. 435/254

FOREIGN PATENT DOCUMENTS 0096388 8/1978 Japan ................................. 435/108
0158193 9/1983 Japan ................................. 435/108

*Primary Examiner*—Elizabeth Weimar
*Attorney, Agent, or Firm*—Oblon, Fisher, Spivak, McClelland & Maier

[57] ABSTRACT

A process for producing L-phenylalanine, which comprises reacting cinnamic acid and an ammonia generator in an aqueous medium in the presence of an enzyme or enzymes from a microorganism belonging to the genus Geotrichum, Moniliella, Syncephalastrum, Endomyces, Aspergillus, Saccharomycopis, Eurotium, Glomerella, Pellicularia or Conatobotyrum, wherein the enzyme or enzymes are capable of producing L-phenylalanine from cinnamic acid and an ammonia generator, and collecting L-phenylalanine from the aqueous medium, is disclosed along with both new and old microorganisms that can be used in the practice of the invention.

16 Claims, No Drawings

PROCESS FOR PRODUCING L-PHENYLALANINE

DETAILED DESCRIPTION OF THE INVENTION

1. Field of the Invention

L-phenylalanine (hereinafter abbreviated as "phenylalanine") is an important starting material for the synthesis of aspartylphenylalanine methyl ester, which is recently receiving special attention as a dipeptide sweetening agent. This invention relates to a process for producing phenylalanine. More particularly it relates to a process for producing phenylalanine from cinnamic acid and an ammonia generator by the aid of microbial action.

2. Discussion of the Background

Methods are known whereby phenylalanine is produced from cinnamic acid and an ammonia generator by the action of enzymes produced by microorganisms. These include a process using species belonging to the genus Rhodotorula or Fusarium (British Pat. No. 1,489,418), a process using species belonging to the genus Sporobolomyces (Japanese Patent Laid-Open No. 96,388, 1978), a process using species belonging to the genus Sporobolomyces or Rhodotorula (Japanese Patent Laid-Open No. 26,197, 1981), and a process using species belonging to the genus Rhodotorula (Japanese Patent Laid-Open No. 18,869, 1984).

However, all of these prior techniques have the disadvantage that cinnamic acid cannot be added to the aqueous medium at a sufficiently high concentration because of the instability of the enzymes produced by the microorganisms against this acid. The result is low concentration of phenylalanine formed in the aqueous medium.

The object of this invention is to provide new microorganisms capable of producing different types of enzymes which are free from the disadvantage of the enzymes produced by the known microorganisms mentioned above (instability against cinnamic acid), thus offering a process for producing phenylalanine from cinnamic acid and an ammonia generator at a higher accumulation rate and higher yield.

SUMMARY OF THE INVENTION

Assiduous studies to find new microorganisms capable of producing new enzymes which are stable against cinnamic acid led us to discover that enzymes produced by species belonging to the genera Geotrichum, Moniliella, Syncephalastrum, Endomyces, Aspergillus, Saccharomycopsis, Eurotium, Glomerella, Pellicuralia and Gonatobotryum have higher stability against cinnamic acid compared with the enzymes produced by the conventionally used microorganisms, and that phenylalanine can be produced from cinnamic acid and an ammonia generator at an outstandingly higher yield and accumulation rate if these new enzymes are employed. This invention was accomplished based on these findings.

DETAILED DESCRIPTION OF THE PREFERRED EMBODIMENTS

Thus this invention relates to a process for producing phenylalanine which comprises allowing a microorganism belonging to the genus Geotrichum, Moniliella, Syncephalastrum, Endomyces, Aspergillus, Saccharomycopsis, Eurotium, Glomerella, Pellicularia or Gonatobotryum and capable of producing phenylalanine from cinnamic acid and an ammonia generator, to act upon cinnamic acid and an ammonia generator in an aqueous medium and collecting phenylalanine thus formed from said aqueous medium.

Typical examples of the microorganisms used in this invention include Geotrichum capitatum AJ-117128 (FERM P-7736, FERM BP-692), Moniliella suaveolens var. suaveolens AJ-117129 (FERM P-7737, FERM BP-693), Syncephalastrum racemosum IFO-4814, Endomyces lindneri AJ-6611 (FERM P-7425, FERM BP-690), Aspergillus chevalieri AJ-7221 (FERM P-7426, FERM BP-691), Saccharomycopsis fibuligera IFO-0105, Eurotium chevalieri IFO-4090, Glomerella tucumanensis AJ-6037 (FERM P-7892, FERM BP-694), Pellicuralia filamentosa. IFO 6254 and Gonatobotryum apiculatum IFO-9098.

The strains FERM P-7736 and FERM P-7737 were originally deposited on July 23, 1984, the strains FERM P-7425 and FERM P-7426 on Feb. 2, 1984, and the strain FERM P-7892 on Oct. 12, 1984, at the Fermentation Research Institute (FRI), Agency of Industrial Science and Technology, 1-3, Migashi 1-chome, Yatabe-machi, Tsukuba-gun, Ibaraki-ken, 305, Japan. These were then converted to deposits under the Budapest Treaty on Jan. 8, 1985, and accorded the corresponding FERM numbers.

Of the microorganisms used in this invention, Geotrichum capitatum AJ-117128 and Moniliella suaveolens var. suaveolens are novel species first discovered by the inventors of this invention.

Geotrichum capitatum has the following micological properties:

(1) Conditions of growth in various culture media (a) Malt extract/agar medium

Ge. capitatum grows favorably in this type of culture medium, forming flat and wet colonies with dull, thick villi. Each colony is hairy in its periphery. It is pure white at the initial stage of cultivation, but turns whitish yellow as cultivation progresses. The backside of each colony is colorless or faint whitish-yellow. Grown hyphae are 2 to 4 $\mu$m wide, have septa, become furcate, and fragment into meristic spores which are oval in shape and 2 to 4×9 $\mu$m in size in most cases. No ascus, ascospore, budding spore or chlamydospore is observed.

(b) Potato/glucose/agar medium

Moderate growth of Ge. capitatum is observed in this type of culture medium. Morphological properties of grown cells are similar to the case with the malt extract/agar medium.

(2) Physiological and ecological properties (a) Optimum growth conditions pH: 5 to 6; temperature: 24° to 27° C.

(b) Allowable range for growth pH: 3 to 9; temperature: up to 35° C.

(3) Assimilability

Assimilability against various substances (1% each added to the bacto-yeast-nitrogen base medium) is listed below (+ represents assimilable substances; — represents non-assimilable substances).

| D-arabinose | — | Ethanol | + |
| --- | --- | --- | --- |
| L-arabinose | — | Inositol | + |
| D-ribose | — | Sorbose | — |
| D-xylose | + | Cellobiose | + |
| D-glucose | + | α-methyl-D-glucoside | — |
| D-mannose | + | Dulcitol | — |
| D-fructose | + | Esculin | + |

| | | | |
|---|---|---|---|
| D-galactose | − | D-melezitose | − |
| L-rhamnose | − | Salicin | + |
| Maltose | + | Erythritol | − |
| Saccharose | + | Glycerol | + |
| Lactose | + | Melibiose | + |
| Trehalose | + | Lactic acid | − |
| D-sorbitol | + | Gluconic acid | + |
| D-mannitol | + | Succinic acid | ± |
| Inulin | ± | 2-Ketogluconic acid | + |
| Dextrin | + | Raffinose (1%) | − |
| Soluble starch | + | Raffinose (4%) | + |
| | | Citric acid | − |

(4) Fermentability

No gas evolution was observed when *Ge. capitatum* was grown in a medium containing 0.45% of yeast extract, 0.75% of peptone and 0.001% of BTB (pH: 6.0) in the presence of each of the following substances (2%):

L-arabinose, D-xylose, D-glucose, D-mannose, D-fructose, D-galactose, maltose, saccharose, trehalose, D-sorbitol, D-mannitol, inositol, glycerol, soluble starch, rhamnose, erythritol, D-ribose, raffinose (1 and 4%), melibiose, cellobiose, esculin, salicin and D-melezitose.

(5) Nitrates assimilability: No
(6) Formation of starch analogues: No
(7) Urea degradability: No
(8) Diazonium Blue B reaction: Negative Based on the micological properties enumerated above, this strain was searched on Illustrated Genera of Imperfect Fungi, 3rd Ed. (Burgess Publishing Company, 1972). As a result of this strain was considered to fall under the category of the genus Geotrichum because of the facts that its cells form meristic conidia consisting of individual or catenulate hyphae, and form no ascospore.

Geotrichum is a family of microorganisms lying intermediate betwenn yeast and fungi, which are treated as yeast or fungi depending on classification system.

We considered it valid to classify this strain as a fungus because cultivation in liquid media caused no turbidity, and made a search on the J. A. von Arx's classification system (Antonie Van Leeuwenhook 43, 333-340, 1970). As a result this was identified as *Geotrichum capitatum* based on the facts that the daily growth rate of colony is less than 1.5 mm and its conidia are cylindrical or oval less than 5 μm in width.

"YEAST: Characteristics and Identification" (J. A. Barnett, Cambridge University, 1983), which classifies Geotrichum as yeast, lists ten species of this genus, but none of them is identical to this strain in the sugar assimilation pattern.

*Moniliella sauveolens* var. *suaveolens* AJ-117129 (FERM P-7737) has the following morphological properties.

This strain grows favorably in the malt/agar culture meidum, forming hairy colonies which are white to whitish yellow in color. This forms meristic and budding spores but no chlamydospore. These morphlogical characteristics are in good agreement with those of *Moniliella suaveolens* var. *suaveolens* listed in Studies in Micology, 19, 1979 (G. S. Dehoog's classification system).

Microbial action

These microorganisms may be allowed to act upon cinnamic aicd and an ammonia generator in either of the following two ways: growing a microorganism in a culture medium and adding cinnamic acid and an ammonia generator during cultivation; or allowing the microbial cells (live or treated cells) to act upon cinnamic acid and an ammonia generator in an aqueous medium.

Commonly used culture media containing carbon sources, nitrogen sources and inorganic ions may be employed for the cultivation of these microorganisms. Further addition of vitamins, amino acids and other organic nutrients in small amounts gives better results in many cases.

Typical examples of the carbon sources include carbohydrates such as glucose and sucrose, organic acids such as acetic acid, and various alcohols. As the nitrogen sources may be mentioned ammonia gas, ammonia water and various ammonium salts. Typical examples of inorganic ions include magnesium, phosphate, potassium and iron ions.

Cultivation should be performed at a controlled pH (2 to 8) and a controlled temperature (15° to 30° C.) over a period of 1 to 30 days.

Phenylalanine can be produced by adding cinnamic acid and an ammonia generator to the culture medium during cultivation. Alternatively, phenylalanine may be produced by dissolving or suspending the microbial cells (live or treated cells) in an aqueous medium containing cinnamic acid and an ammonia generator and allowing the solution or suspension to stand (with stirring when desired) while maintaining the temperature at a suitable level between 10° and 70° C.

There is no limitation on the amount of cinnamic acid used, but its preferable concentration is 0.01 to 1.0M (most preferably 0.1 to 0.8M) when the reaction is carried out in the batch process. With the conventionally used microorganisms, the preferred amount of cinnamic acid is 0.1 to 0.2M, because higher concentrations result in lower yields of phenylalanine. The microorganisms of this invention, on the contrary, have higher stability against cinnamic acid and can be added to the culture medium in higher concentrations, thus leading to larger amounts of accumualted phenylalanine. When the column process using immobilized cells is employed, somewhat lower concentration of cinnamic acid is preferable than in the batch process.

The ammonia generator, which is a second substrate, is preferably supplied in the form of an ammonium salt, such as ammonium acetate, chloride and sulfate. It should be used in an amount larger than cinnamic acid on molar basis, preferably in large excess. These substrates may also be added in portions as the reaction proceeds.

The reaction is carried out in an aqueous medium at a temperature of 20° to 60° C., preferably 30° to 40° C., and at a pH of 7 to 12, preferably 9 to 11.

As the live microbial cells, the culture liquid in which the microorganism has been grown may be used without any treatment. Alternatively, the cells separated from the culture liquid may be employed after or without washing. As the treated cells, may be used mechanically mashed cells, cells treated with ultrasonic waves, acetone-dried cells, cells treated with lysozyme or other enzyme, cells treated with a surface-active agent, toluene or the like, or protein fraction isolated from the microbial cells.

In some cases, addition of a small amount of at least one member selected from cinnamic acid, phenylalanine and D-phenylalanine to a culture medium creates microbial cells having higher ability to produce phenylalanine from cinnamic acid and an ammonia generator.

Identification and determination of phenylalanine was performed by the bioassay using *Leuconostoc mesenteroides* ATCC-8042.

EXAMPLE 1

A liquid culture media containing 1.0 g/dl of polypeptone, 1.0 g/dl of yeast extract 0.3 g/dl of $K_2HPO_4$, 0.1 g/dl of $KH_2PO_4$, 0.05% of $MgSO_4.7H_2O$ and 0.5 g/dl of L-phenylalanine (pH: 6.0, 50 ml) was placed in a 500 ml flask and sterilized at 115° C. for 15 minutes.

*Syncephalastrum racemosum* IFO-4814, *Endomyces lindneri* AJ-6611 (FERM P-7425, FERM BP-690), *Aspergillus chevalieri* AJ-7221 (FERM P-7426, FERM BP-691), *Saccharomycopsis fibuligera* IFO-0105, *Eurotium chevalieri* IFP-4090, *Pellicuralia filamentosa* IFO 6254 and *Gonatobotryum apiculatum* IFO-9098 (each previously grown in a potato dextrose/agar medium at 25° C. for seven days) were each inoculated to the liquid culture medium prepared above and cultivated at 25° C. for seven days. The grown microbial cells, collected from each medium by filtration, were added to 100 ml of an aqueous solution containing 1.0 g/dl of cinnamic acid and 55 ml/dl of 28% ammonia water (pH controlled to 10.0 with hydrochloric acid) to a concentration of 5 g/dl, and the reaction was continued at 30° C. for 24 hours. The amount of accumulated L-phenylalanine was 240 mg/dl for *Syncephalastrum racemosum*, IFO 4814 800 mg/dl for *Endomyces lindneri* AJ6611 FERM P-7425, 110 mg/dl for *Aspergillus chevalieri* AJ7221 FERM P-7426, 720 mg/dl for *Saccharomycopsis fibuligera* IFO 0105, 310 mg/dl for *Eurotium chevalieri* IFO 4090, 490 mg/dl for *Pellicuralia filamentosa* IFO 6254, and 370 mg/dl for *Gonatobotryum apiculatum* IFO 9098.

EXAMPLE 2

A liquid culture medium containing 1.0 g/dl of polypeptone, 1.0 g/dl of yeast extract, 0.3 g/dl of $K_2HPO_4$, 0.1 g/dl of $KH_2PO_4$, 0.05 g/dl of $MgSO_4.7H_2O$ and 0.5 g/dl of L-phenylalanine (pH: 6.0, 50 ml) was placed in a 500 ml flask and sterilized at 115° C. for 15 minutes.

The strains AJ-117128 (FERM P-7736, FERM BP-692) and AJ-117129 (FERM P-7737, FERM BP-693), each previously grown in a malt extract/agar medium at 25° C. for seven days, were inoculated to the liquid medium prepared above and grown at 25° C. for 14 days, and the strain AJ-6307 (FERM P-7892, FERM BP-694), previously grown in a malt extract/agar medium at 25° C. for four days, was inoculated to the liquid medium and grown at 25° C. for four days. The grown microbial cells, collected from each medium by filtration and washed with physiological saline, were added to 100 ml of an aqueous solution containing 55 ml/dl of 28% ammonia water and a varying amount of cinnamic acid as shown in Table 1 (pH controlled to 10.5 with hydrochloric acid) to a concentration of 20 g/dl, and the reaction was continued at 30° C. for 72 hours. The amounts of accumulated L-phenylalanine are listed in Table 1.

TABLE 1

| Cinnamic Acid (g/dl) | Amount of phenylalanine | | |
|---|---|---|---|
| | AJ-17128 | AJ-117129 | AJ-6307 |
| 1 | 0.8 | 0.8 | 0.9 |
| 2 | 1.6 | 1.6 | 1.8 |
| 4 | 3.2 | 2.5 | 3.6 |

TABLE 1-continued

| Cinnamic Acid (g/dl) | Amount of phenylalanine | | |
|---|---|---|---|
| | AJ-17128 | AJ-117129 | AJ-6307 |
| 5 | 3.9 | 3.0 | 4.1 |
| 6 | 4.1 | 3.3 | 4.7 |

EXAMPLE 3

A liquid culture medium containing 1.0 g/dl of polypeptone, 1.0 g/dl of yeast extract, 0.3 g/dl of $K_2HPO_4$, 0.1 g/dl of $KH_2PO_4$, 0.05 g/dl of $MgSO_4\ 7H_2O$ and 0.5 g/dl of L-phenylalanine (pH: 6.0, 50 ml) was placed in a 500 ml flask and sterilized at 115° C. for 15 minutes.

The strain IFO-4814, previously grown in a potato dextrose/agar medium at 25° C. for seven days, was inoculated to the liquid medium prepared above and grown at 25° C. for three days by the shake method; the strain AJ-117128 (FERM P-7736, FERM BP-692), previously grown in a malt extract/agar medium at 25° C. for 14 days, was inoculated to the liquid medium and grown at 25° C. for eight days by the shake method; and the strains AJ-6307 (FERM P-7892, FERM BP-694), IFO 6254 and IFO-9098, each previously grown in a malt extract/agar medium at 25° C. for five days, were inoculated to the liquid medium and grown at 25° C. for three days by the shake method. To each of the culture liquid was added a solution of 5 g/dl cinnamic acid in an aqueous solution of 5 g/dl $(NH_4)_2SO_4$ and ammonia (pH: 7.0), and cultivation was continued for an additional 48 hours. The amounts of phenylalanine accumulated in the culture liquid are listed in Table 2.

TABLE 2

| Amounts of Phenylalanine Formed (mg/dl) | |
|---|---|
| IFO-4814 | 84 |
| AJ-117128 | 134 |
| AJ-6307 | 156 |
| IFO-6254 | 132 |
| IFO-9098 | 124 |

EXAMPLE 4

One gram of microbial cells of *Syncephalastrum racemosum* IFO-4814, grown by the method described in Example 1, and one gram each of microbial cells of AJ-117128 (FERM P-7736, FERM BP-693) and AJ-6307 (FERM P-7892, FERM BP-694) grown by the method described in Example 2, were each suspended in 4 ml of deionized water. After cooling on ice, 750 mg of acrylamide and 45 mg of methylene-bisacrylamide were dissolved in each suspension, the oxygen was completely displaced by introducing nitrogen gas, 3.5 mg of ammonium persulfate and 8 μl of N,N'-dimethylaminopropionitrile were added, and the mixture was allowed to stand under ice cooling. After one hour, the cell-containing gel thus formed was collected by filtration through a 50-mesh metal gauze and washed with physiological saline. Two grams of the immobilized cells thus obtained were added to an aqueous solution containing 2.0 g/dl of cinnamic acid and 5.5 ml of 28% ammonia (pH controlled to 10.5 with hydrochloric acid), and the reaction was continued at 30° C. for 24 hours. The amounts of phenylalanine formed are listed in Table 3.

TABLE 3

| Amounts of Phenylalanine Formed (mg/dl) | |
| --- | --- |
| IFO-4814 | 40 |
| AJ-117128 | 224 |
| AJ-6307 | 520 |

EXAMPLE 5

Microbial cells (0.5 g) of *Endomyces lindneri* AJ-6611 (FERM P-7425, FERM BP-690), grown and washed by the same manner as Example 1, and microbial cells (0.5 g each) of AJ-117129 (FERM P-7737, FERM BP-693) and AJ-6307 (FERM P-7892, FERM BP-694), grown and washed in the same manner as Example 2, were each put in a dialysis membrane (0.6 cm in diameter; Visking Company), and the two ends were tightly closed by tying with strings, forming a bag containing the microbial cells. It was immersed in 10 ml of an aqueous solution containing 2 g/dl of cinnamic acid and 55 ml/dl of 28% ammonia (pH controlled to 10.5 with hydrochloric acid), and the reaction was continued at 30° C. for 24 hours for AJ-6611 and at 30° C. for 72 hours for the others. The amounts of phenylalanine formed in the reaction solution are listed in Table 4.

TABLE 4

| Amounts of Phenylalanine Formed (mg/dl) | |
| --- | --- |
| AJ-6611 | 750 |
| AJ-117129 | 1440 |
| AJ-6307 | 1820 |

What is claimed is:

1. A process for producing L-phenylalanine, which comprises:
    reacting cinnamic acid and an ammonia generator in an aqueous medium in the presence of a microorganism belonging to the genus Geotrichum, Moniliella, Syncephalastrum, Endomyces, Aspergillus, Saccharomycopis, Eurotium, Glomerella, Pellicularia or Conatobotyrum, and
    collecting L-phenylalanine from said aqueous medium.

2. The process of claim 1, wherein said aqueous medium is a culture medium containing said microorganism.

3. A process of claim 1, wherein the concentration of cinnamic acid is from 0.01 to 1.0M.

4. The process of claim 3, wherein said concentration is from 0.1 to 0.8M.

5. The process of claim 3, wherein said concentration is greater than 0.2M.

6. The process of claim 1, wherein the ammonia generator is an ammonium salt.

7. The process of claim 6, wherein said salt is ammonium acetate, ammonium chloride, or ammonium sulfate.

8. The process of claim 1, wherein a temperature of from 10° to 70° C. is used in said reacting step.

9. The process of claim 1, wherein the microorganism is immobilized.

10. The process of claim 1, comprising carrying out the reaction at a temperature of from 20° to 60° C.

11. The process of claim 1, comprising carrying out the reaction at a temperature of from 30° to 40° C.

12. The process of claim 1, comprising using a microorganism belonging to the genus Geotrichum or Moniliella.

13. The process of claim 1, comprising using a microorganism belonging to the genus Syncephalastrum or Endomyces.

14. The process of claim 1, comprising using a microorganism belonging to the genus Aspergillus or Saccharomycopis.

15. The process of claim 1, comprising using a microorganism belonging to the genus Eurotium or Glomerella.

16. The process of claim 1, comprising using a microorganism belonging to the genus Pellicularia or Conatobotyrum.

* * * * *